United States Patent [19]

Andree

[11] 4,137,561
[45] Jan. 30, 1979

[54] MAGNIFYING HAND TOOL WITH SELF-CONTAINING ILLUMINATING MEANS

[76] Inventor: George C. Andree, 528 Willow St., West Hempstead, N.Y. 11552

[21] Appl. No.: 764,832

[22] Filed: Feb. 2, 1977

[51] Int. Cl.² ........................................... F21V 33/00
[52] U.S. Cl. ................................................. 362/119
[58] Field of Search ................... 240/2 E, 2 M, 6.46, 240/6.4 R, 2 MT, 2 MA, 2.18, 10.6 R, 41.15, DIG. 3; 32/7, 40 R, DIG. 7; 350/243, 244, 235; 338/119, 196

[56] References Cited

U.S. PATENT DOCUMENTS

| | | | |
|---|---|---|---|
| 1,780,231 | 11/1930 | Hardy | 240/2 MA |
| 2,316,301 | 4/1943 | Ullman | 240/2 M |
| 2,712,584 | 7/1955 | Pantages | 338/196 |
| 3,655,960 | 4/1972 | Andree | 240/2 E |

*Primary Examiner*—J. D. Miller
*Assistant Examiner*—Peter S. Wong
*Attorney, Agent, or Firm*—Leonard H. King

[57] ABSTRACT

A hand tool having integral work area illumination means and magnifying means capable of being held and adjusted by one hand of the user. The apparatus may be powered by internal batteries or from an external source by means of an adapter.

2 Claims, 4 Drawing Figures

MAGNIFYING HAND TOOL WITH SELF-CONTAINING ILLUMINATING MEANS

BACKGROUND OF THE INVENTION

This invention relates to an instrument which combines means for both illuminating a work area and magnifying its image, and is capable of being adjusted and hand held by a single hand.

In applicant's prior patent, U.S. Pat. No. 3,655,960, issued Apr. 11, 1972, there is disclosed an instrument useful in the graphic arts where there is a continuous requirement for making detailed corrections to negatives, plates and art work by removal of unwanted portions, adding images not present in the original work, repairing portions which were not properly produced in the original. While applicant's prior device has been most suitable for such purposes, experience with the apparatus has indicated that it may be useful in many other fields, e.g. in the medical field it may be used for minor surgery, such as operations on warts, callouses, splinters, imbedded pieces of glass and even for removal of objects from the eye. For such critical paths, the prior art apparatus has certain limitations, which the present improvement overcomes. The improved apparatus disclosed hereinafter has also wide application in other fields and has been found successful for preparing electron microscope slides for use as a dissecting tool in biology labs and in the assembly of components in the electronic and mechanical fields.

The improved device disclosed hereinafter is provided with a much more convenient adjusting means facilitating one hand operation and also has provision for varying the intensity of the illumination.

SUMMARY OF THE INVENTION

In accordance with the present invention there has been provided an instrument comprising an elongated support member having a cavity therein. A light emitting device, such as a small incandescent bulb, is positioned at one end of the cavity. The remainder of the cavity being adapted to contain a battery for energizing the light device or, in the alternative, a battery simulator, which replaces the battery and is energized from a conventional AC power source through a transformer and a rheostat so that the apparatus may be plugged into a conventional wall outlet yet permit variation of the light intensity without interference with the handling characteristics of the tool. A light transmitting means is affixed to one end of the support member and contains a light emitting device such as the incandescent lamp and a tool holding means. A magnifying lens is supported by a rack & pinion system for adjustable positioning of the magnifying means relative to the work area.

A tool such as a brush, pen, cutting knife, scribe or other instrument is inserted in the tool holding means, which may be the slip-chuck of conventional design.

The second end of the light transmitting means has an inner concave surface which focuses the light transmitted through the light transmitting means from the light emitting device therein substantially corresponding with the tip of the tool. The magnifying lens, which may be translated parallel to the longitudinal axis of the core member and also pivoted in any direction of one or more universal joints, is positioned by the user so that the work is illuminated at all times.

The above description, as well as further objects, features and advantages of the present invention, will be more fully appreciated by reference to the following detailed description of a presently preferred, but nonetheless illustrative, embodiment in accordance with the present invention when taken in conjunction with the accompanying drawings.

DESCRIPTION OF THE PREFERRED EMBODIMENT

Figure 1:
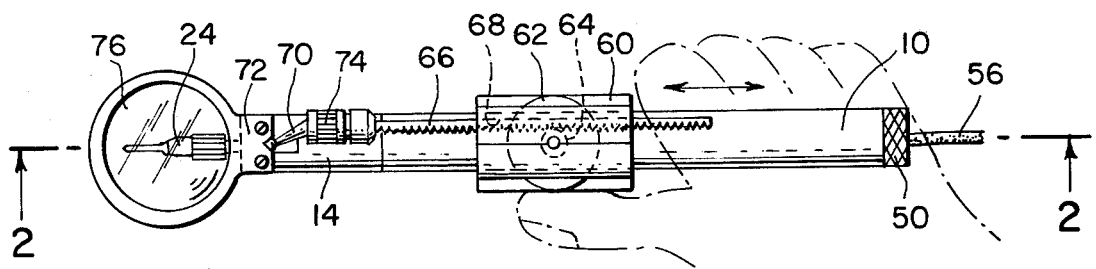
FIG. 1 is a top plan view of the apparatus of this invention.

Referring to the drawing, the instrument comprises of an elongated hollow electrically conducting metal cylinder 10 having an internally threaded end portion 12 and a second threaded end 13. A cylindrical light transmitting lens element 14 is provided with a thread 15 which mates with thread 13. A cavity 16 receives a light bulb 18, sleeve 19 of the bulb makes electrical contact to metal cylinder 10 through metal disc 20 in which the sleeve 19 sits in a contact relationship.

Figure 4:
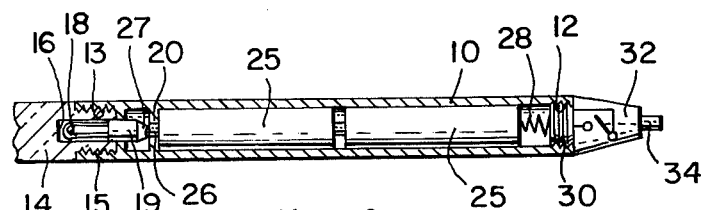
FIG. 4 shows a battery with switch means, which may be used in place of the AC power supply.

The outer end of the lens 14 is provided with a roughened face surface so that the light transmitted through the body of the lens is directed outwardly. This is a characteristic of many light transmitting resins such as Polymethylmethacrylate. On the other hand, the end of the lens may be polished in the shape of a concave disc so as to direct the light forward. At the center of the lens a bore 22 is provided, preferably of a tapered configuration, for receiving tapered shanks 23 of tools 24. In order to energize the incandescent lamp, two batteries 25, 25' in series such as shown in FIG. 4 may be employed wherein the positive contact 26 of the forward battery 25' makes contact with the center contact 27 on the bulb 18 and the conventional negative terminal of the rearward battery 25 makes contact to spring 28 connected to threaded metal portion 30 and, in turn, to the case 10. Within knob 32 there is provided a switch (shown schematically) and actuated by contact button 34.

Figure 2:
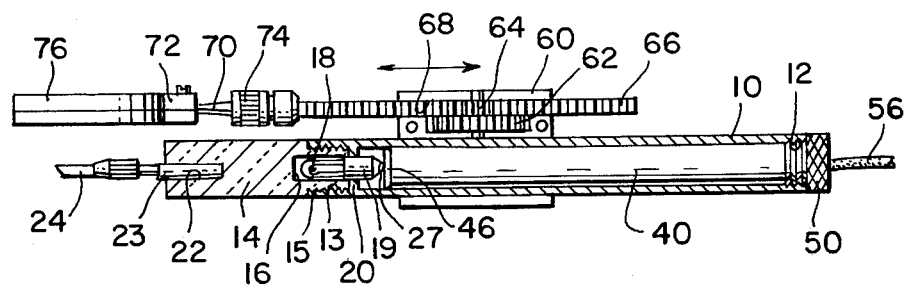
FIG. 2 is a section taken along line 2—2 of FIG. 1.
Figure 3:
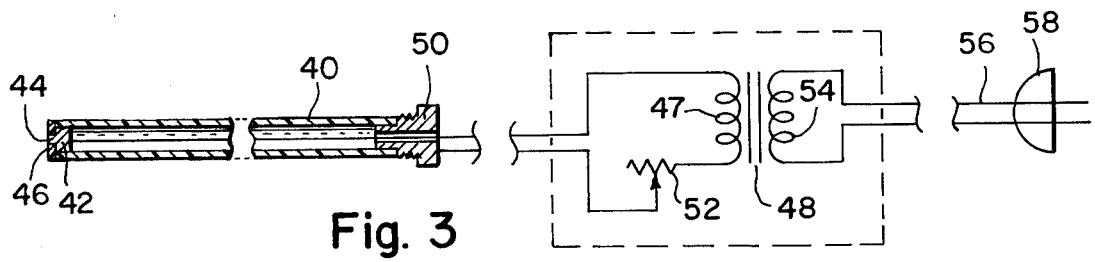
FIG. 3 is a sectional view of a battery simulator in conjunction with a schematic drawing of an electrical supply for energizing the apparatus.

In FIG. 2, however, there is shown a battery simulator of FIG. 4 which consists of a non-conductive tube 40 which terminates in a metal contact button 42 having a central portion 44 surrounded by insulation 46. One lead runs from member 42 to one side of the secondary 47 of transformer 48, shown schematically.

Another lead is connected to metal terminal member 50 through a rheostat 52, which permits adjusting the voltage applied to the bulb whereby the intensity of the illumination provided may be varied.

The Primary 54 of transformer 48 is connected through a conventional power cord 56 and plug 58, to a conventional source of line current. Thus, it will be appreciated, that the apparatus may be used either with batteries or from an AC source.

Mounted onto the elongated metal cylinder 10, there is provided a housing 60, which contains a drive wheel 62 extending to the side of the instrument, whereby the user holding the instrument in his hand can readily actuate the device, the drive wheel, with his thumb. On a common shaft with the drive wheel 62 there is provided a pinion 64 which engages a rack 66, which lies in a groove 68 in the housing 60.

Shaft 70 terminates at both ends in a ball configuration which is secured by ball joint clamping means 72 and 74, permitting adjustment of the magnifying means 76, attached to member 72 to be adjusted to any desired configuration or position.

While there have been shown and described and pointed out the fundamental novel features of the invention as applied to a preferred embodiment thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. A hand tool having integral illumination means, adjustable magnification means, a chuck for receiving interchangeable workpiece modifying tool elements;

and a hollow cylindrical elongated support member adapted to be held in the crook of the hand having electrically energizable illumination means at one end thereof with a terminal means extending into the support member;

the improvement comprising:
   (a) a bracket affixed to said support member;
   (b) a shaft rotatably mounted in said bracket perpendicular to said support member;
   (c) a thumbwheel fixed to said shaft rotatably mounted in said bracket, said thumbwheel having diametrically opposed portions extending from said bracket;
   (d) a pinion gear carried by said shaft above said thumbwheel relative to said support member;
   (e) a rack above said thumbwheel translatably secured to said bracket engaging said pinion gear and carrying said magnification means for adjustably positioning same, said rack arranged to move parallel to said support member.

2. The hand tool of claim 1, including contact making means adapted to be inserted in said hollow cylindrical elongated support member and make electrical contact with said illumination means and external variable voltage control means connected to said contact making means, said control means having provision for connection to an external power source.

* * * * *